US00PP33243P2

(12) United States Plant Patent
Gomez Bullis

(10) Patent No.: US PP33,243 P2
(45) Date of Patent: Jul. 6, 2021

(54) ***NEOREGELIA* PLANT NAMED 'GAIA'**

(50) Latin Name: ***Neoregelia carolinae* X *(Neoregelia princeps* X *Neoregelia hybrida)***
Varietal Denomination: Gaia

(71) Applicant: Patricia E. Gomez Bullis, Princeton, FL (US)

(72) Inventor: Patricia E. Gomez Bullis, Princeton, FL (US)

(73) Assignee: BULLIS BROMELIADS, Princeton, FL (US)

( * ) Notice: Subject to any disclaimer, the term of this patent is extended or adjusted under 35 U.S.C. 154(b) by 0 days.

(21) Appl. No.: 16/974,078

(22) Filed: Sep. 22, 2020

(51) Int. Cl.
*A01H 5/02* (2018.01)
*A01H 6/22* (2018.01)

(52) U.S. Cl.
USPC ..... Plt./370
CPC ..... *A01H 6/22* (2018.05)

(58) Field of Classification Search
USPC ..... Plt./370
CPC ..... A01H 6/22; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Neoregelia* plant named 'Gaia', characterized by its broad and outwardly arching growth habit; leaves that are arching and recurved in aspect; leaves that are light yellow green in color with distinct dark green-colored outer stripes and margins; upper leaves are red purple in color when flower development commences; and good interiorscape and landscape performance.

2 Drawing Sheets

Botanical designation: *Neoregelia carolinae* X (*Neoregelia princeps* X *Neoregelia hybrida*).
Cultivar denomination: 'GAIA'.

BACKGROUND OF THE INVENTION

The present invention relates to a new and distinct cultivar of *Neoregelia* plant, botanically known as *Neoregelia carolinae* X (*Neoregelia princeps* X *Neoregelia hybrida*), and hereinafter referred to by the name 'Gaia'.

The new *Neoregelia* plant is a product of a planned breeding program conducted by the Inventor in Princeton, Fla. The objective of the breeding program is to create new *Neoregelia* plants with uniquely colored leaves.

The new *Neoregelia* plant originated from a cross-pollination made by the Inventor in 2010 in Princeton, Fla. of an unnamed proprietary selection of *Neoregelia carolinae*, not patented, as the female, or seed, parent with an unnamed proprietary selection of *Neoregelia princeps* X *Neoregelia hybrida*, not patented, as the male, or pollen, parent. The new *Neoregelia* plant was discovered and selected by the Inventor as a single plant within the progeny of the stated cross-pollination in a controlled greenhouse environment in Princeton, Fla. in 2011.

Asexual reproduction of the new *Neoregelia* plant by offsets in a controlled environment in Princeton, Fla. since 2011, has shown that the unique features of this new *Neoregelia* plant are stable and reproduced true to type in successive generations.

SUMMARY OF THE INVENTION

Plants of the new *Neoregelia* have not been observed under all possible combinations of environmental conditions and cultural practices. The phenotype may vary somewhat with variations in environment conditions such as temperature and light intensity without, however, any variance in genotype.

The following traits have been repeatedly observed and are determined to be the unique characteristics of 'Gaia'. These characteristics in combination distinguish 'Gaia' as a new and distinct *Neoregelia* plant:

1. Broad and outwardly arching growth habit.
2. Leaves that are arching and recurved in aspect.
3. Leaves that are light yellow green in color with distinct dark green-colored outer stripes and margins; upper leaves are red purple in color when flower development commences.
4. Good interiorscape and landscape performance.

Plants of the new *Neoregelia* differ primarily from plants of the female parent selection in the following characteristics:

1. Leaves of plants of the new *Neoregelia* are more arching than and not as horizontal as leaves of plants of the female parent selection.
2. Upper leaves of plants of the new *Neoregelia* develop red purple coloration when flowering whereas upper leaves of plants of the female parent selection are reddish orange when flowering.
3. Plants of the new *Neoregelia* and the female parent selection differ in leaf color as leaves of plants of the new *Neoregelia* are at least 80% light yellow green in color whereas leaves of plants of the female parent selection are 50% light yellow green in color.

Plants of the new *Neoregelia* differ primarily from plants of the male parent selection in the following characteristics:

1. Upper leaves of plants of the new *Neoregelia* develop red purple coloration when flowering whereas upper leaves of plants of the male parent selection are dark pink when flowering.

2. Plants of the new *Neoregelia* and the male parent selection differ in leaf color as leaves of plants of the new *Neoregelia* have a broader light yellow green-colored area and fewer dark green-colored stripes than leaves of plants of the male parent selection.

Plants of the new *Neoregelia* can be compared to plants of the *Neoregelia carolinae* X *Neoregelia princeps* 'Mendoza', disclosed in U.S. Plant Pat. No. 22,584. In side-by-side comparisons, plants of the new *Neoregelia* and 'Mendoza' differ primarily in the following characteristics:

1. Leaves of plants of the new *Neoregelia* are more arching than and not as upright as leaves of plants of 'Mendoza'.
2. Plants of the new *Neoregelia* and 'Mendoza' differ in leaf color as leaves of plants of the new *Neoregelia* are at least 80% light yellow green in color whereas leaves of plants of 'Mendoza' are 50% pale yellow green in color.

BRIEF DESCRIPTION OF THE PHOTOGRAPHS

The accompanying colored photographs illustrate the overall appearance of the new *Neoregelia* plant showing the colors as true as it is reasonably possible to obtain in colored reproductions of this type. Colors in the photographs may differ slightly from the color values cited in the detailed botanical description which accurately describe the colors of the new *Neoregelia* plant.

The photograph on the first sheet is a top perspective view of a typical flowering plant of 'Gaia' grown in a container.

The photograph on the second sheet is a close-up view of a typical flowering plant of 'Gaia'.

DETAILED BOTANICAL DESCRIPTION

The aforementioned photographs and following observations, measurements and values describe flowering plants grown during the spring in 15-cm containers in a polypropylene-covered greenhouse in Princeton, Fla. and under cultural practices typical of commercial *Neoregelia* production. During the production of the plants, day temperatures ranged from 18° C. to 30° C., night temperatures ranged from 18° C. to 22° C. and light levels about 2,500 foot-candles. Plants were 14 months old when the photographs and description were taken. In the following description, color references are made to The Royal Horticultural Society Colour Chart, 2015 Edition, except where general terms of ordinary dictionary significance are used.

Botanical classification: *Neoregelia carolinae* X (*Neoregelia princeps* X *Neoregelia hybrida*) 'Gaia'.

Parentage:

*Female, or seed, parent*.—Unnamed proprietary selection of *Neoregelia carolinae*, not patented.

*Male, or pollen, parent*.—Unnamed proprietary selection of *Neoregelia princeps* X *Neoregelia hybrida*, not patented.

Propagation:

*Type*.—By offsets.

*Time to initiate roots, summer*.—About 30 to 45 days at ambient temperatures about 28° C. to 30° C.

*Time to initiate roots, winter*.—About 45 to 60 days at ambient temperatures about 28° C. to 30° C.

*Time to produce a rooted young plant, summer*.—About three months at ambient temperatures about 28° C. to 30° C.

*Time to produce a rooted young plant, winter*.—About four months at ambient temperatures about 18° C. to 22° C.

*Root description*.—Fine, fibrous; typically brown to beige in color, actual color of the roots is dependent on substrate composition, water quality, fertilizer type and formulation, substrate temperature and physiological age of roots.

*Rooting habit*.—Moderately freely branching; sparse.

Plant description:

*Plant and growth habit*.—Broad and outwardly arching growth habit; leaves in rosettes; plants readily produce uniform offsets; vigorous growth habit.

*Plant height*.—About 14.5 cm.

*Plant diameter or spread*.—About 41 cm.

*Internode length*.—About 2 mm.

*Stem diameter at the soil level*.—About 2.5 cm.

*Stem texture*.—Smooth, glabrous.

*Stem color*.—Close to NN155A.

Leaf description:

*Arrangement*.—Rosette, spiral phyllotaxis; simple; sessile, clasping.

*Shape*.—Narrowly oblong with broader sheathing base.

*Apex*.—Cuspidate to short aristate.

*Base*.—Truncate, clasping.

*Margin*.—Serrate, spinose.

*Length*.—About 2.8 cm.

*Width, mid-section*.—About 4.5 cm.

*Width, towards the base*.—About 6.5 cm.

*Texture and luster, upper and lower surfaces*.—Smooth, glabrous; leathery; narrowly and longitudinally ribbed; glossy, shiny.

*Venation pattern*.—Parallel.

*Color*.—Lower leaves, upper surface: At least 80% of the center of the leaf, closest to 151B; towards the base, fading to close to 146D; margins and apex, close to 147A; occasional longitudinal stripes, close to 144A and 146A; venation, similar to lamina colors. Lower leaves, lower surface: At least 80% of the center of the leaf, closest to 151B tinged with close to 146A; towards the base, fading to close to 146C; margins and apex, close to 147A; occasional longitudinal stripes, close to 144A and 146A; venation, similar to lamina colors. Upper leaves, upper surface: Close to 53A; venation, close to 53A; margins and apex, close to 147A. Upper leaves, lower surface: Close to 53A and 53B; venation, close to 53A and 53B; margins and apex, close to 147A.

Inflorescence description:

*Inflorescence form*.—Terminal flat-topped compact corymb located inside the leaf rosette; about 48 flowers develop per inflorescence.

*Time to flower*.—Plants begin flowering about 60 to 80 days weeks after planting; plants flower naturally during the spring in Florida.

*Flower longevity*.—Individual flowers last about two to three days on the plant; flowers persistent.

*Fragrance*.—None detected.

*Inflorescence height*.—About 2.5 cm.

*Inflorescence diameter*.—About 3 cm.

*Flower size*.—Length: About 2.5 cm. Diameter: About 6 mm.

*Petals*.—Quantity per flower: Three in a single whorl. Shape, free part: Lanceolate. Apex: Sharply acuminate. Base: Truncate, fused at the base. Margin:

Entire. Length: About 2.25 cm. Width at base of free part: About 3 mm. Texture and luster, upper and lower surfaces: Smooth, glabrous; slightly glossy. Color: When opening and fully opened, upper (inner) surface: Close to 93C; towards the base, close to NN155D. When opening and fully opened, lower (outer) surface: Close to 93B; towards the base, close to NN155D.

*Flower bracts*.—Quantity per flower: One. Shape: Narrowly and elongated deltoid. Length: About 2 cm. Width: About 5 mm. Texture, upper and lower surfaces: Membranous and translucent. Color, upper and lower surfaces: Close to 145D.

*Sepals*.—Not observed on plants of the new *Neoregelia*.

*Peduncles*.—Length: About 2.5 cm. Diameter: About 1 cm. Strength: Strong. Aspect: Typically erect. Texture: Smooth, glabrous. Color: Close to NN155D.

*Pedicels*.—Length: About 6 mm. Diameter: About 3 mm. Strength: Strong. Aspect: Depending on position in the inflorescence, typically erect to outward and curving upright. Texture: Smooth, glabrous. Color: Close to 157A.

*Stamens*.—Quantity per flower: Six. Filament length: About 1 cm; partially adnate to the petals. Filament color: Close to NN155D. Anther shape: Lanceolate. Anther length: About 2 mm. Anther color: Close to 158C. Pollen amount: None observed.

*Pistils*.—Quantity per flower: One. Pistil length: About 1.25 cm. Stigma shape: Elongated oblong. Stigma color: Close to 157C. Style length: About 8 mm. Style color: Close to NN155D. Ovary color: Close to 155A to 155B.

*Fruits and seeds*.—To date, fruit and seed production have not been observed on plants of the new *Neoregelia*.

Temperature tolerance: Plants of the new *Neoregelia* have been observed to tolerate temperatures ranging from about 2° C. to about 37° C.

Interior & garden performance: Plants of the new *Neoregelia* have been observed to have good postproduction longevity under interior conditions, to have good garden performance and to tolerate temperatures ranging from 2° C. to 37° C.

Pathogen & pest resistance: To date, resistance to pathogens and pests common to *Neoregelia* plants has not been observed.

It is claimed:

1. A new and distinct *Neoregelia* plant named 'Gaia' as illustrated and described.

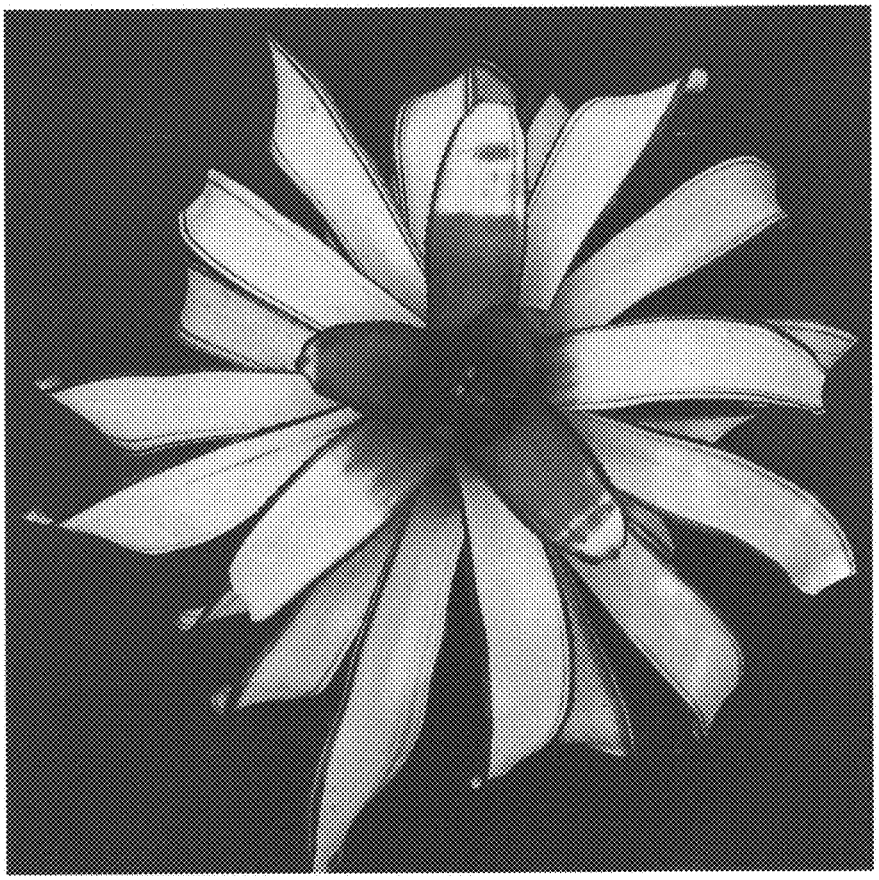

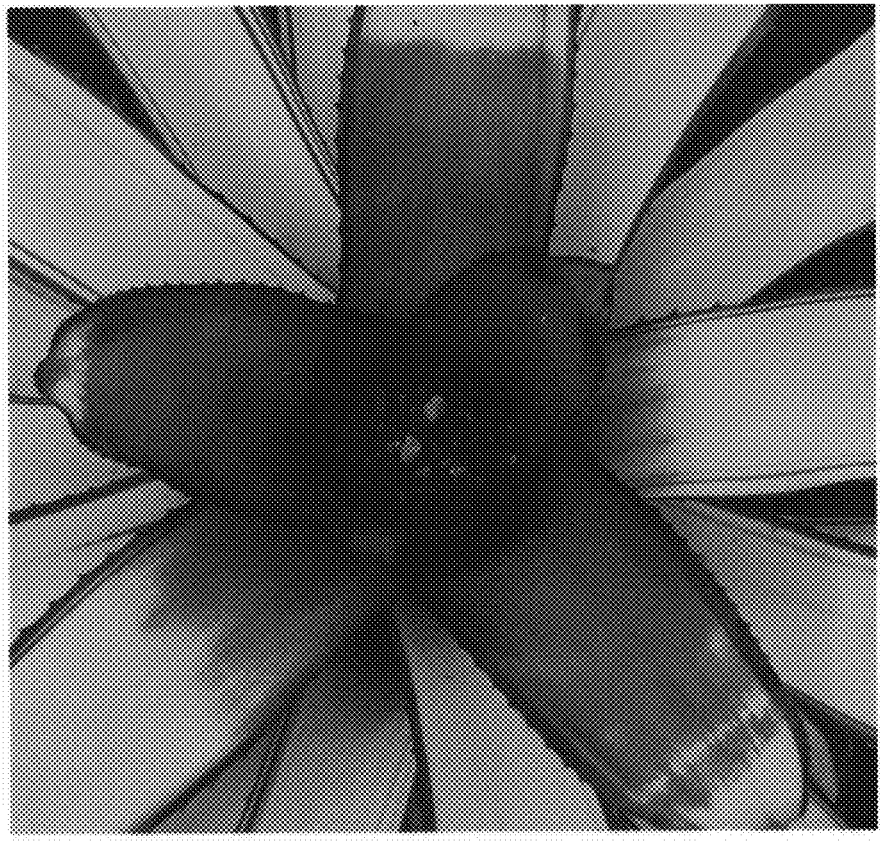

* * * * *